United States Patent

Ammermann et al.

[11] Patent Number: 5,827,861
[45] Date of Patent: Oct. 27, 1998

[54] FUNGICIDAL MIXTURES

[75] Inventors: Eberhard Ammermann, Heppenheim; Gisela Lorenz, Hambach; Dietrich Mappes, Westheim; Klaus Schelberger, Gönnheim; Manfred Hampel, Neustadt, all of Germany

[73] Assignee: BASF Aktiengesellschaft, Ludwigshafen, Germany

[21] Appl. No.: 750,809

[22] PCT Filed: May 27, 1995

[86] PCT No.: PCT/EP95/02025

§ 371 Date: Dec. 10, 1996

§ 102(e) Date: Dec. 10, 1996

[87] PCT Pub. No.: WO95/34203

PCT Pub. Date: Dec. 21, 1995

[30] Foreign Application Priority Data

Jun. 10, 1994 [DE] Germany .......................... 44 20 278.4

[51] Int. Cl.⁶ .......................... A01N 37/12; A01N 37/44; A01N 43/64
[52] U.S. Cl. .............................. 514/383; 514/539
[58] Field of Search ..................... 514/383, 539

[56] References Cited

U.S. PATENT DOCUMENTS

| 4,829,085 | 5/1989 | Wenderoth et al. ..................... 514/522 |
| 5,317,027 | 5/1994 | Sauter et al. ........................... 514/399 |

FOREIGN PATENT DOCUMENTS

| 253 213 | 1/1988 | European Pat. Off. . |
| 254 426 | 1/1988 | European Pat. Off. . |
| 531 837 | 3/1993 | European Pat. Off. . |
| 2 267 644 | 12/1993 | United Kingdom . |
| 93/22921 | 11/1993 | WIPO . |

OTHER PUBLICATIONS

Chem. Abstr. vol. 118, No. 23, Jun. 7, 1993, 118:228112.
Resesarch Disclosure Nr. 338, 1992 Havant GB, Disclosure 33893.

*Primary Examiner*—Allen J. Robinson
*Attorney, Agent, or Firm*—Keil & Weinkauf

[57] ABSTRACT

A fungicidal mixture containing
a) an oxime ether carboxylic acid ester of the formula Ia or Ib and
b) 1-(1,2,4-triazol-1-yl)-2-cyano-2-(4-chlorophenyl) hexane II

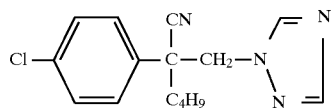

in a synergistically active amount is described.

9 Claims, No Drawings

FUNGICIDAL MIXTURES

This application is a 371 of PCT/EP95/02025 filed May 27, 1995.

The present invention relates to a fungicidal mixture which contains a) an oxime ether carboxylic acid ester of the formula Ia or Ib

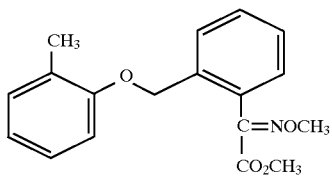

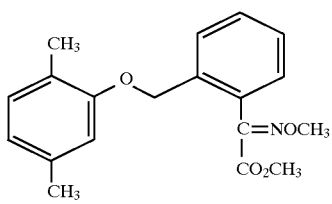

and b) 1-(1,2,4-triazol-1-yl)-2-cyano-2-(4-chlorophenyl) hexane II

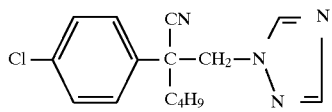

in a synergistically active amount.

The invention additionally relates to methods of controlling harmful fungi using mixtures of the compounds I and II and the use of the compound I and the compound II for the production of mixtures of this type.

The compound of the formula I (or Ia or Ib), its preparation and its action against harmful fungi are disclosed in the literature (EP-A 253 213). The compound II (common name: myclobutanil), its preparation and its action against harmful fungi are likewise known.

With respect to a decrease in the application rates and an improvement of the spectrum of action of known compounds, the present invention is based on mixtures which, with a reduced total amount of applied active compounds, have an improved action against harmful fungi (synergistic mixtures).

Accordingly, the mixtures defined at the beginning have been found. It has additionally been found that on simultaneous joint or separate application of the compound I and the compound II or on application of the compound I and the compound II in succession harmful fungi can be controlled better than with the individual compounds.

The compounds of the formulae I and II can be present in the E or the Z configuration with respect to the C=N double bond (with respect to the carboxylic acid function group). Accordingly, it can be used in the mixture according to the invention in each case either as the pure E or Z isomer or as an E/Z isomer mixture. The E/Z isomer mixture or the E isomer is preferably used, the E isomer being particularly preferred in the case of the compound I.

Because of the basic character of the N group, the compound II is able to form salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having 1 to 20 carbon atoms), arylsulfonic acids or—disulfonic acids (aromatic radicals such as phenyl and naphthyl which carry one or two sulfonic acid groups), alkylphosphonic acids (phosphonic acids having straight-chain or branched alkyl radicals having 1 to 20 carbon atoms), arylphosphonic acids or—diphosphonic acids (aromatic radicals such as phenyl and naphthyl which carry one or two phosphonic acid radicals), the alkyl and aryl radicals being able to carry further substituents, eg. p-toluene-sulfonic acid, salicylic acid, p-aminosalicylic acid, 2-phenoxy-benzoic acid, 2-acetoxybenzoic acid, etc.

Suitable metal ions are in particular the ions of the elements of the second main group, in particular calcium and magnesium, of the third and fourth main group, in particular aluminum, tin and lead, as well as of the first to eighth subgroup, in particular chromium, manganese, iron, cobalt, nickel, copper, zinc and others. The metal ions of the elements of the subgroups of the fourth period are particularly preferred. The metals can in this case be present in the different valencies applicable to them.

Preferably, the pure active compounds I and II are employed in the preparation of the mixtures, to which, if required, further active compounds against harmful fungi or other pests such as insects, arachnids or nematodes, or alternatively herbicidal or growth-regulating active compounds or fertilizers, can be admixed.

The mixtures of the compounds I and II and the simultaneous joint or separate use of the compounds I and II are distinguished by an outstanding action against a wide spectrum of phytopathogenic fungi, in particular from the Ascomycetes and Basidiomycetes class. In some cases they are systemically active and can therefore also be employed as foliar and soil fungicides.

They have particular importance for the control of a multiplicity of fungi on various crop plants such as cotton, vegetable plants (eg. cucumbers, beans and cucurbits), barley, grass, oats, coffee, maize, fruit plants, rice, rye, soybeans, grapes, wheat, decorative plants, sugar cane and a multiplicity of seeds.

In particular, they are suitable for the control of the following phytopathogenic fungi: Erysiphe graminis (powdery mildew) on cereals, Erysiphe cichoracearum and Sphaerotheca fuliginea on cucurbits, Podosphaera leucotricha on apples, Uncinula necator on vines, Puccinia species on cereals, Rhizoctonia species on cotton and lawns, Ustilago species on cereals and sugar cane, Venturia inaequalis (scab) on apples, Helminthosporium species on cereals, Septoria nodorum on wheat, Botrytis cinerea (gray mold) on strawberries and vines, Cercospora arachidicola on groundnuts, Pseudocercosporella herpotrichoides on wheat and barley, Pyricularia oryzae on rice, Phytophthora infestans on potatoes and tomatoes, Plasmopara viticola on vines, Alternaria species on vegetables and fruit and also Fusarium and Verticillium species.

They are additionally applicable in the protection of materials (eg. wood preservation), for example against Paecilomyces variotii.

The compounds I and II can be applied simultaneously jointly or separately, or in succession, the sequence in the case of separate application in general having no effect on the control success.

The compounds I and II are customarily applied in a weight ratio of from 10:1 to 0.1:1, preferably from 5:1 to 0.2:1, in particular from 5:1 to 1:1.

Depending on the type of effect desired, the application rates of the mixtures according to the invention are from 0.01 to 3 kg/ha, preferably from 0.1 to 1.5 kg/ha, in particular from 0.1 to 1.0 kg/ha. The application rates here for the compound I are from 0.01 to 0.5 kg/ha, preferably from 0.05 to 0.5 kg/ha, in particular from 0.05 to 0.4 kg/ha. The application rates for the compound II are correspondingly from 0.01 to 0.5 kg/ha, preferably from 0.05 to 0.5 kg/ha, in particular from 0.05 to 0.4 kg/ha.

In the treatment of seed, application rates of mixture of from 0.001 to 50 g/kg of seed, preferably from 0.01 to 10 g/kg, in particular from 0.01 to 8 g/kg, are in general used.

If harmful fungi which are pathogenic for plants are to be controlled, the separate or joint application of the compounds I and II or of the mixtures of the compounds I and II is carried out by spraying or dusting the seeds, the plants or the soils before or after sowing of the plants or before or after emergence of the plants.

The fungicidal synergistic mixtures according to the invention and the compounds I and II can be prepared, for example, in the form of directly sprayable solutions, powders and suspensions or in the form of high-percentage aqueous, oily or other suspensions, dispersions, emulsions, oil dispersions, pastes, dusting compositions, broadcasting compositions or granules and applied by spraying, atomizing, dusting, broadcasting or watering. The application form is dependent on the intended use; it should in each case guarantee a dispersion of the mixture according to the invention which is as fine and uniform as possible.

The formulations are prepared in a manner known per se, eg. by addition of solvents and/or carriers. Inert additives such as emulsifiers or dispersants are customarily admixed to the formulations.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols or fatty alcohol glycol ethers, condensation products of sulfonated naphthalene and its derivatives with formaldehyde, condensation products of naphthalene or of naphthalene-sulfonic acids with phenol and formaldehyde, polyoxyethylene octylphenol ethers, ethoxylated isooctyl-, octyl- or nonylphenol, alkylphenol or tributylphenyl polyglycol ethers, alkylaryl polyether alcohols, isotridecyl alcohol, fatty alcoholethylene oxide condensates, ethoxylated castor oil, polyoxyethylene or polyoxy-propylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the compound I or II or the mixture of the compounds I and II with a solid carrier.

Granules (eg. coated, impregnated or homogeneous granules) are customarily prepared by binding the active compound or the active compounds to a solid carrier.

Fillers or solid carriers used are, for example, mineral earths such as silica gel, silicic acids, silicates, talc, kaolin, limestone, lime, chalk, bole, loess, clay, dolomite, diatomaceous earth, calcium and magnesium sulfate, magnesium oxide, ground plastics, and fertilizers such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.1 to 95% by weight, preferably from 0.5 to 90% by weight, of one of the compounds I and II or the mixture of the compounds I and II. The active compounds are in this case employed in a purity of from 90% to 100%, preferably from 95% to 100% (according to NMR spectrum or HPLC).

The compounds I and II and the mixtures or the corresponding formulations are applied by treating the harmful fungi or the plants, seeds, soils, surfaces, materials or spaces to be kept free from them with a fungicidally active amount of the mixture, or of the compounds I and II in the case of separate application. Application can be carried out before or after attack by the harmful fungi.

Examples of the synergistic action of the mixtures according to the invention against harmful fungi The fungicidal action of the compounds and of the mixtures could be shown by the following tests:

The active compounds were prepared separately or together as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and accordingly diluted to the desired concentration with water.

Assessment was carried out by determination of the attacked leaf areas in percent. These percentage values were converted to efficiencies.

The efficiencies to be expected of the active compound mixtures were determined by the Colby formula [R. S. Colby, Weeds 15 (1967), 20–22] and compared with the observed efficiencies.

Colby formula:

$$E = x + y - xxy/100$$

E efficiency to be expected, expressed in % of the untreated control, when using the mixture of the active compounds A and B in the concentrations a and b x the efficiency, expressed in % of the untreated control, when using the active compound A in the concentration a y the efficiency, expressed in % of the untreated control, when using the active compound B in the concentration b In the case of an efficiency of 0, the attack on the treated plants corresponds to that of the untreated control plants; in the case of an efficiency of 100%, the treated plants exhibited no attack.

Activity against Botrytis cinerea (gray mold)

Paprika seedlings (variety: Neusiedler Ideal Elite) having 4–5 leaves were sprayed with the active compound preparation until dripping wet. After drying off, the plants were sprayed with the conidia suspension of the fungus Botrytis cinerea and kept for 5 days at 22°–24° C. at high atmospheric humidity. Assessment was carried out visually.

In this test, 1:1 mixtures of the compounds Ia and II (total application rate of the mixtures 5 ppm or 2.5 ppm) showed efficiencies of 100 or 90% respectively, the expected efficiencies being 88 or 76% respectively. The untreated control plants were attacked to 90%.

We claim:

1. A fungicidal mixture containing a) an oxime ether carboxylic acid ester of the formula Ia or Ib

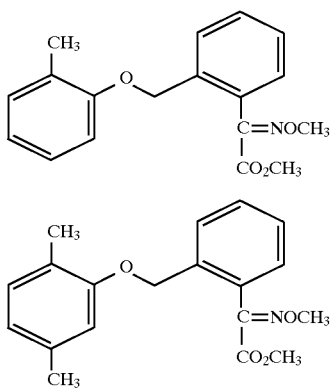

and b) 1-(1,2,4-triazol-1-yl)-2-cyano-2-(4-chlorophenyl)hexane of the formula II

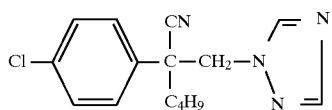

in a synergistically active amount.

2. A fungicidal mixture as defined in claim 1, wherein the weight ratio of the compound Ia or Ib to the compound II is from 10:1 to 0.1:1.

3. A fungicidal mixture as claimed in claim 2 wherein the weight ratio of the compounds Ia or Ib to the compound II is 5:1 to 0.2:1.

4. A fungicidal mixture as claimed in claim 3 wherein the weight ratio of the compounds Ia or Ib to the compound II is 5:1 to 1:1.

5. A fungicidal mixture as claimed in claim 4 wherein the weight ratio of the compounds Ia or Ib to the compound II is 1:1.

6. A method of controlling harmful fungi, which comprises treating the harmful fungi, their environment or the plants, seeds, soils, surfaces, materials or spaces to be kept free from said fungi with a synergistically effective amount of the compound of the formula Ia or Ib as defined in claim 1 and the compound of the formula II as defined in claim 1.

7. The method of claim 6, wherein the compound of the formula Ia or Ib and the compound of the formula II are applied simultaneously jointly or separately, or in succession.

8. The method of claim 6, wherein from 0.01 to 0.5 kg/ha of the compound of the formula Ia or Ib are applied.

9. The method of claim 6, wherein from 0.01 to 0.5 kg/ha of the compound of the formula II are applied.

* * * * *